United States Patent [19]

Yamada et al.

[11] Patent Number: 5,008,188

[45] Date of Patent: * Apr. 16, 1991

[54] PROCESS FOR PRODUCING S-ADENOSYL-L-HOMOCYSTEINE

[75] Inventors: Hideaki Yamada; Yoshiki Tani; Sakayu Shimizu, all of Kyoto; Shozo Shiozaki, Kawasaki, all of Japan

[73] Assignee: Nippon Zeon Co., Ltd., Tokyo, Japan

[ * ] Notice: The portion of the term of this patent subsequent to Aug. 12, 2003 has been disclaimed.

[21] Appl. No.: 117,439

[22] Filed: Nov. 4, 1987

Related U.S. Application Data

[63] Continuation of Ser. No. 578,769, Feb. 9, 1984, abandoned.

[30] Foreign Application Priority Data

Feb. 10, 1983 [JP] Japan ................................... 58-28807

[51] Int. Cl.$^5$ ...................... C12P 14/40; C12P 13/12; C12P 19/18
[52] U.S. Cl. ........................................ 435/88; 435/43; 435/45
[58] Field of Search ...................... 435/85, 87, 88, 110, 435/113, 116

[56] References Cited

U.S. PATENT DOCUMENTS

| 3,183,170 | 5/1965 | Kitai et al. | 435/110 |
|---|---|---|---|
| 4,080,259 | 3/1978 | Boesten et al. | 195/2 |
| 4,518,692 | 5/1985 | Rozzell | 435/116 |
| 4,605,625 | 8/1986 | Yamada et al. | 435/280 |

FOREIGN PATENT DOCUMENTS

| 2540886 | 8/1984 | France | 45/88 |
|---|---|---|---|
| 0146596 | 8/1984 | Japan | 435/88 |

OTHER PUBLICATIONS

Walker et al., "S-Adenosylhomocysteine Metabolism in Various Species" Canadian Journal of Biochemistry vol. 53 pp. 312-319 (1975).
Shapiro, "Biosynthesis of Methionine from Homocysteine and S-Methylmethionine in Bacteria" Journal of Bacteriology 72 pp. 730-735 (1956).
Cantoni et al., "Activation of Methionine for Transmethylation" Journal of Biological Chemistry 225 pp. 1033-1048 (1957).
Shimizu, H. et al., (1984) Agric. Biol. Chem., vol. 48(5), pp. 1383-1385.
Chabannes, et al., "S-Adenosyl-L-Homocysteine: Simplified Enzyme Preparation With High Yield", Prep. Biochem. 12(5) pp. 395-415 (1983) Chemical Abstracts 98: 194538y.
Archives of Biochemistry & Biophysics, 69, 575 (1962), J. A. Duerre/F. Schlen, "Formation and Metabolism of S-Adenosyl-L-Homocysteine in Yeast".
J. Biol. Chem., 240, 2521 (1965), S. K. Shapiro, et al., "Biosynthesis of Methionine in *Saccharomyces cerevisiae*".

Primary Examiner—Douglas W. Robinson
Assistant Examiner—Irene Marx
Attorney, Agent, or Firm—Sherman and Shalloway

[57] ABSTRACT

Process for producing S-adenosyl-L-homocysteine, which comprises reacting adenosine with homocysteine by contacting them in an aqueous medium in the presence of cells or treated cells of a microorganism of a specified genus having the ability to synthesize S-adenosyl-L-homocysteine from adenosine and homocysteine, and collecting the S-adenosyl-L-homocysteine synthesized.

17 Claims, No Drawings

PROCESS FOR PRODUCING S-ADENOSYL-L-HOMOCYSTEINE

This application is a continuation of application Ser. No. 578,769 filed Feb. 9, 1984, now abandoned.

This invention relates to a process for enzymatically synthesizing S-adenosyl-L-homocysteine efficiently from adenosine and homocysteine using cells or treated cells of a microorganism as an enzyme source, and collecting the synthesized product.

S-Adenosyl-L-homocysteine (to be abbreviated SAH hereinafter) is an important biologically active substance formed by a methyl group donating reaction in vivo in which S-adenosyl methionine (to be abbreviated SAM) participates. In recent years, SAH has been found to be efficacious as a sedative and a sleep inducing agent, and is desired to be produced in quantities.

Conventional methods for producing SAH include, for example, extraction from yeasts of the genus Saccharomyces or Candida [for example, Arh. Biochem. Biophys, 69, 575 (1962)], enzymatic demethylation of SAM [for example, J. Biol. Chem., 240, 2512 (1965)], and chemical demethylation of SAM (for example, U.S. Pat. No. 3,642,772). These methods, however, are very costly and are not industrially feasible.

A method is also known to synthesize adenosine and homocysteine enzymatically in the presence of a cell-free extract of a yeast of the genus Saccharomyces or Candida [for example, Arch. Biochem. Biophys, 69, 575 (1962)]. The types of microorganisms which can be used in this method, however, are restricted, and it has been desired to detect other useful microorganisms by screening.

In view of the above state of art, the present inventors worked extensively on the enzymatic synthesis of SAH. This work has now led to the discovery that when certain specified microorganisms are used, SAH can be synthesized efficiently whether they are in the form of a cell-free extract, crushed cells, resting cells or dried cells.

Thus, according to this invention, there is provided a process for producing SAH, which comprises reacting adenosine with homocysteine by contacting them in an aqueous medium in the presence of cells or treated cells of a microorganism having the ability to synthesize SAH from adenosine and homocysteine, said microorganism being a bacterium belonging to the genus Enterobacter, Agrobacterium, Micrococcus, Corynebacterium, Arthrobacter, Brevibacterium, Chromobacterium, Xanthomonas, Rhodopseudomonas, Pseudomonas, Alcaligenes, Acinetobacter, Flavobacterium, Cellulomonas, Protaminobacter, or Azotobacter; a yeast belonging to the genus Saccharomycopsis, Schizosaccharomyces, Pichia, Hansenula, Schwanniomyces, Debaryomyces, Saccharomycodes, Hanseniaspora, Lipomyces, Sporobolomyces, Kluyveromyces, Cryptococcus, Torulopsis, Kloeckera, Wickerhamia, Torula, Rhodotorula, Trichosporon, Oosporidium or Lodderomyces, a mold fungus belonging to the genus Mucor, Rhizopus, Absidia, Aspergillus, Penicillium, Monascus, Neurospora, Aureobasidium, Fusarium, Gibberella, Arthroderma, Sporothrix, Verticillium, Gliocladium, Trichophyton, Phytophthora, Eurotium or Cylindrocarpon; an actinomycete belonging to the genus Streptomyces, Mycobacterium, Nocardia, Streptoverticillium, Micromonospora, Micropolyspora, Streptosporangium or Microellobosporia; or a basidiomycete belonging to the genus Gloeophyllum, Shizolphyllum, Trametes, Laetiporus, Lentinus, Lyophyllum, Pycnoporus or Lepista, and collecting SAH synthesized.

The microorganism used as a source of enzyme in this invention may be any microorganism which belongs to the above genera and in the form of cells or treated cells, has the ability to synthesize SAH from adenosine and homocysteine. Specific examples include bacteria such as Enterobacter cloacae IFO 13535,
Agrobacterium tumefaciens IFO 13265,
Micrococcus luteus IFO 3333,
Corynebacterium fascians IFO 12077,
Arthrobacter globiformis IFO 12137,
Brevibacterium protophormiae IFO 12128,
Chromobacterium iodinum IFO 3558,
Xanthomonas campestris IFO 13303,
Rhodopseudomonas spheroides IFO 12203,
Pseudomonas putida IFO 12996,
Pseudomonas dacunhae IFO 12048,
Pseudomonas aeruginosa IFO 3445,
Alcaligenes faecalis IFO 12669,
Alcaligenes faecalis IFO 13111,
ATCC 17705,
Acinetobacter calcoaceticus IFO 12552,
Flavobacterium gasogenes IFO 12065,
Cellulomonas flavigena IFO 3753,
Azotobacter vinelandii IFO 12018, and
Protaminobacter ruber IFO 3708;
yeasts such as
Saccharomycopsis fibuligera IFO 0103,
Shizosaccharomyces pombe IFO 0346,
Pichia farinosa IFO 0459,
Hansenula silvicola IFO 0807,
Schwanniomyces occidentalis IFO 0371,
Debaryomyces castellii IFO 1359,
Saccharomycodes ludwigii IFO 0798,
Hanseniaspora valbyensis IFO 0115,
Lipomyces lipofer IFO 0673,
Sporobolomyces holsaticus IFO 1034,
Kluyveromyces thermotolerans IFO 0662,
Cryptococcus neoformans IFO 0410,
Torulopsis candida IFO 0380,
Kloeckera apiculata IFO 0151,
Wickerhamia fluorescens IFO 1116,
Torula dematia IFO 6216,
Rhodotorula glutinis IFO 0389,
Trichosporon cutaneum IFO 1198,
Oosporidium margaritiferum IFO 1208, and
Lodderomyces elongisporus IFO 1676;
mold fungi such as
Mucor subtilissimus IFO 6338,
Rhizopus oryzae IFO 5440,
Absidia corymbifera IFO 4009,
Aspergillus terreue IFO 6346,
Penicillium expansum IFO 5854,
Monascus anka IAM 8001,
Monascus ruber IFO 9203,
Monascus serorubescens IFO 4487,
Neurospora crassa IFO 6067,
Aureobasidium pullulans IFO 6405,
Fusarium culmorum IFO 5902,
Gibberella fujikuroi IFO 6605,
Arthroderma uncinatum IFO 7865,
Sporothrix schenckii IFO 5983,
Verticillium albo-atrum IFO 5922,
Gliocladium deliguescens IFO 6617,

*Trichophyton mentagrophytes* IFO 5809,
*Phytophthora infestans* IFO 9173, and
*Cylindrocarpon destructans* IFO 5998;
actinomycetes such as
*Streptomyces hygroscopicus* IFO 3192,
*Streptomyces griseolus* IFO 3403,
*Mycobacterium phlei* IFO 3158
*Nocardia asteroides* IFO 3424,
*Streptoverticillium kentuchense* IFO 12880,
*Micromonospora coerules* IFO 13504,
*Micropolyspora angiospora* IFO 13155,
*Streptosporangium roseum* IFO 3776, and
*Microellobosporia violacea* IFO 12517; and
basidiomycetes such as
*Gloeophyllum trabeum* IFO 6430,
*Shizolphyllum commune* IFO 6504,
*Trametes gibbosa* IFO 4946,
*Laetiporus sulphureus* IFO 6497,
*Lentinue edodes* IFO 8340,
*Lyophyllum decastes* IFO 30161,
*Pycnoporus coccineus* IFO 9768, and
*Lepista nuda* IFO 30139.

Any natural or artificial mutants of these strains may be used in this invention if they have the ability to synthesize SAH.

The process for synthesizing SAH in accordance with this invention utilizes the action of an endocellular enzyme in the form of the cells of a microorganism or the treated product of these cells. The enzyme can be prepared by cultivating the microorganism in a customary manner. Cultivation may be carried out in an ordinary medium containing a carbon source, a nitrogen source, inorganic salts and traces of organic nutrient sources. The medium may be chosen properly depending upon the kind of the microorganism. The cultivation is usually carried out in a liquid medium, but it may also be carried out on a solid surface. The cultivation conditions can be properly chosen depending upon the kind of the microorganism. The cultivation may be carried out usually at a temperature of 15° to 80° C. and a pH of 3 to 12, preferably at a temperature of 20° to 45° C. and a pH of 4 to 9, for 10 to 120 hours. The growth of the microorganism may be promoted by performing aeration and stirring during the cultivation.

In the reaction of synthesizing SAH in accordance with this invention, the microorganism cultivated as above is used in the form of cells or treated cells. For example, the reaction of synthesizing SAH proceeds even when the cells in the culture broth of the microorganism are used directly. When the components in the culture broth cause hazards or when it is desired to use large amounts of the cells, it is preferred to use cells separated from the culture broth. Resting cells may fully serve for the purpose. But for convenience of storage or handling, they may be used as air-dried cells, lyophilized cells and acetone-treated cells. They can also be used in the form of treated cells such as crushed cells and a cell-free extract. Alternatively, the cells or cell-treated products may be used after fixing them in a customary manner.

In accordance with the process of this invention, adenosine and homocysteine as substrates for enzymatic reaction are contacted with each other in an aqueous medium in the presence of the cells or treated cells of the microorganism. Homocysteine used in the reaction may be an L-isomer or a DL-isomer. The concentrations of the substrates are usually at least 1 mM, preferably 10 to 500 mM, for adenosine and at least 1 mM, preferably 10 to 500 mM, for homocysteine. It should be understood that the term 'homocysteine' as used herein also includes substances which yield homocysteine in the reaction system, for example homocystine and homocysteine thiolactone.

The pH of the reaction system in the SAH synthesizing reaction is 4 to 12, preferably 6 to 10. The pH can be adjusted by ordinary methods, for example by using potassium phosphate buffer, Tris buffer, ammonium chloride buffer, and glycine buffer, etc.

The reaction temperature may be one at which the reaction proceeds well and which does not affect the activity of the enzyme, the substrates and the product. Usually, it is 15° to 60° C., preferably 20° to 50° C. The reaction time may be prescribed so that the conversion of the substrates to SAH increases. In the batchwise process, the reaction time is usually 0.1 to 48 hours, preferably 0.5 to 36 hours. For some purposes, organic solvents such as acetone and ethanol or various surfaceactive agents may be added to the aqueous medium used in the reaction.

SAH may be recovered in a customary manner from the reaction mixture containing synthesized SAH. One method comprises contacting the SAH-containing reaction mixture with a strongly acidic cation exchange resin to cause adsorption of SAH, and eluting the resin with sulfuric acid, adding phosphotungstic acid to the eluate to precipitate SAH. Another method comprises contacting the SAH-containing reaction mixture with activated carbon to cause adsorption of SAH, eluting the activated carbon with phenol/water/conc. aqeuous ammonia (50:50:1), concentrating the eluate under reduced pressure, adjusting the pH of the concentrate to 7 with acetic acid, and thereafter crystallizing SAH at 0° C.

The following Examples illustrate the present invention more specifically. It should be understood however that the invention is in no way limited to these examples.

In the following examples, SAH was quantitatively determined by the following method.

Immediately after the end of the reaction, the reaction mixture was cooled to 0°-5° C., and perchloric acid was added to stop the reaction. The insoluble materials were removed by centrifugation. To the resulting supernatant liquid, potassium phosphate buffer (pH 7.0) was added. The resulting potassium perchlorate was removed by centrifugation. A predetermined amount of the supernatant liquid was sampled, and the quantity of SAH therein was determined by high-performance liquid chromatography (Model 638-30 made by Hitachi Limited; column Cosmocil 5 $C_{18}$; detector UV 260 nm).

EXAMPLE 1

One platinum loopful of each of the bacterial strains indicated in Table 1 which had been cultivated at 28° C. for 24 hours in an agar slant culture medium (pH 7.0) composed of 1 g/dl of glucose, 1.5 g/dl of peptone, 0.3 g/dl of yeast extract 0.3 g/dl of $K_2HPO_4$, 0.2 g/dl of NaCl, 0.02 g/dl of $MgSO_4.7H_2O$ and 2 g/dl of agar was inoculated in 10 ml of a heat-sterilized liquid medium composed of 1 g/dl of glucose, 1.5 g/dl of peptone, 0.3 g/dl of yeast extract, 0.3g/dl of $K_2HPO_4$, 0.2 g/dl of NaCl and 0.02 g/dl of $MgSO_4.7H_2O$ and adjusted to pH 7.0, and cultivated with shaking at 28° C. for 40 hours. The cells were collected by centrifugation, washed with 0.1M potassium phosphate buffer (pH 8.0), suspended in 1 ml of a substrate solution consisting of 10 mM of adenosine, 10 mM of DL-homocysteine and 100 mM of potassium phosphate buffer (pH 8.0). The suspension was shaken at 30° C. for 1 hour to perform the reaction. The results are shown in Table 1.

TABLE 1

| Bacterial strain | Yield of SAH (micromols/ml) |
| --- | --- |
| Pseudomonas putida IFO 12996 | 2.07 |
| Enterobacter cloacae IFO 13535 | 0.80 |
| Agrobacterium tumefaciens IFO 13265 | 0.03 |
| Micrococcus luteus IFO 3333 | 0.05 |
| Corynebacterium fascians IFO 12077 | 0.17 |
| Arthrobacter globiformis IFO 12137 | 0.31 |
| Brevibacterium protophormiae IFO 12128 | 0.04 |
| Chromobacterium iodinum IFO 3558 | 0.03 |
| Xanthomonas campestris IFO 13303 | 0.11 |
| Rhodopseudomonas spheroides IFO 12203 | 0.87 |
| Alcaligenes faecalis IFO 12669 | 0.93 |
| Alcaligenes faecalis IFO 13111 | 0.89 |
| Pseudomonas dacunhae IFO 12048 | 0.66 |
| Pseudomonas aeruginosa IFO 3445 | 1.97 |
| Acinetobacter calcoaceticus IFO 12552 | 0.54 |
| Flavobacterium gasogenes IFO 12065 | 0.31 |
| Cellulomonas flavigena IFO 3753 | 0.07 |
| Azotobacter vinelandii IFO 12018 | 0.14 |
| Protaminobacter ruber IFO 3708 | 0.20 |

EXAMPLE 2

One platinum loopful of each of the yeast strains indicated in Table 2 which had been cultivated at 28° C. for 48 hours in an agar-slant culture medium (pH 6.0) composed of 5 g/dl of glucose, 0.5 g/dl of peptone, 0.1 g/dl of yeast extract, 0.2 g/dl of $KH_2PO_4$, 0.1 g/dl of $K_2HPO_4$, $MgSO_4.7H_2O$ and 2 g/dl of agar was inoculated in 10 ml of a heat-sterilized liquid culture medium composed of 5 g/dl of glucose, 0.5 g/dl of peptone, 0.1 g/dl of yeast extract, 0.2 g/dl of $KH_2PO_4$, 0.1 g/dl of $K_2HPO_4$ and 0.02 g/dl of $MgSO_4.7H_2O$ and adjusted to pH 6.5, and cultivated with shaking at 28° C. for 40 hours. The cells were collected by centrifugation, washed with 0.1M potassium phosphate buffer (pH 8.0), and suspended in 1 ml of a substrate solution composed of 10 mM of adenosine, 10 mM of DL-homocysteine and 100 mM of potassium phosphate buffer (pH 8.0). The suspension was shaken at 30° C. for 2 hours to perform reaction. The results are shown in Table 2.

TABLE 2

| Yeast strain | Amount of SAH yielded (micromol/ml) |
| --- | --- |
| Saccharomycopsis fibuligera IFO 0103 | 0.17 |
| Schizosaccharomyces pombe IFO 0346 | 0.60 |
| Sporobolomyces holssaticus IFO 1034 | 0.60 |
| Pichia farinosa IFO 0459 | 0.14 |
| Hansenula silvicola IFO 0807 | 0.08 |
| Schwanniomyces occidentalis IFO 0371 | 0.14 |
| Debaryomyces castellii IFO 1359 | 0.03 |
| Saccharomycodes ludwigii IFO 0798 | 0.01 |
| Hanseniaspora valbyensis IFO 0115 | 0.11 |
| Lipomyces lipofer IFO 0673 | 0.08 |
| Kluyveromyces thermotolerans IFO 0662 | 0.14 |
| Cryptococcus neoformans IFO 0410 | 0.04 |
| Torulopsis candida IFO 0380 | 0.29 |
| Kloeckera apiculata IFO 0151 | 0.03 |
| Wickerhamia fluorescens IFO 1116 | 0.19 |
| Torula dematia IFO 6216 | 0.04 |
| Rhodotorula glutinis IFO 0389 | 0.11 |
| Trichosporon cutaneum IFO 1198 | 0.19 |
| Oosporidium margaritiferum IFO 1208 | 0.03 |
| Lodderomyces elongisporus IFO 1676 | 0.20 |

EXAMPLE 3

Using cells of each of the mold fungus strains indicated in Table 3 which had been cultivated in the same way as in Example 2, collected by filtration and washed with physiological saline, the same reaction as in Example 2 was carried out except that the reaction time was changed as shown in Table 3. The amounts of SAH yielded are shown in Table 3.

TABLE 3

| Mold fungus strain | Reaction time (hr) | Amount of SAH yielded (micromol/ml) |
| --- | --- | --- |
| Mucor subtilissimus IFO 6338 | 4.5 | 0.06 |
| Rhizopus oryzae IFO 5440 | 4.5 | 0.54 |
| Absidia corymbifera IFO 4009 | 4.5 | 0.41 |
| Aspergillus terreus IFO 6346 | 2 | 0.03 |
| Penicillilum expansum IFO 5854 | 4 | 0.44 |
| Monascus ruber IFO 9203 | 4.5 | 0.88 |
| Monascus serorubescens IFO 4487 | 4.5 | 0.70 |
| Neurospora crassa IFO 6067 | 4 | 1.36 |
| Aureobasidium pullulans IFO 6405 | 4 | 0.25 |
| Fusarium culmorum IFO 5902 | 4.5 | 1.54 |
| Gibberella fujikuroi IFO 6605 | 2 | 1.61 |
| Arthroderma uncinatum IFO 7865 | 4 | 0.13 |
| Sporothrix schenckii IFO 5983 | 4 | 0.32 |
| Verticillium albo-atrum IFO 5922 | 4 | 0.19 |
| Gliocladium deliquescens IFO 6617 | 4.5 | 1.24 |
| Trichophyton mentagrophytes IFO 5809 | 2 | 0.03 |
| Phytophthora infestans IFO 9173 | 2 | 0.04 |
| Cylindrocarpon destructans IFO 5998 | 2 | 0.08 |

EXAMPLE 4

One platinum loopful of cells of each of the actinomycetes indicated in Table 4 which had been cultivated at 28° C. for 48 hours in an agar slant culture medium (pH 7.2) composed of 0.2 g/dl of yeast extract, 1 g/dl of soluble starch and 2 g/dl of agar was inoculated in 10 ml of a heat-sterilized liquid culture medium composed of 1 g/dl of peptone, 0.5 g/dl of meat extract, 0.1 g/dl of yeast extract and 0.5 g/dl of NaCl and adjusted to pH 7.1, and cultivated with shaking at 28° C. for 40 hours. The culture broth was worked up in the same way as in Example 1 to obtain cells. Using the resulting cells, the same reaction as in Example 1 was carried out except that the reaction time was changed to 2 hours. The results are shown in Table 4.

TABLE 4

| Actinomycetes strain | Amount of SAH yielded (micromol/ml) |
| --- | --- |
| Mycobacterium phlei IFO 3158 | 0.05 |
| Nocardia asteroides IFO 3424 | 0.06 |
| Streptomyces griseolus IFO 3403 | 2.27 |
| Streptoverticillium kentuchense IFO 12880 | 2.32 |
| Micromonospora coerulea IFO 13504 | 3.24 |
| Micropolyspora angiospora IFO 13155 | 4.00 |
| Streptosporandium roseum IFO 3776 | 0.87 |
| Microellobosporia violacea IFO 12517 | 3.58 |
| Streptomyces hygroscopicus IFO 3192 | 3.40 |

EXAMPLE 5

One platinum loopful of cells of each of basidiomycetes indicated in Table 5 which had been cultivated at 28° C. for 96 hours in an agar slant culture medium (pH 5.0) composed of 2 g/dl of glucose, 0.3 g/dl of yeast extract, 0.3 g/dl of peptone, 0.1 g/dl of $KH_2PO_4$, 0.05 g/dl of MgSO$_4$.7H$_2$O and 2 g/dl of agar was inoculated in 10 ml of a heat-sterilized liquid culture medium composed ob 2 g/dl of glucose, 0.3 g/dl of yeast extract, 0.3 g/dl of peptone, 0.1 g/dl of KH$_2$PO$_4$ and 0.05 g/dl of MgSO$_4$.7H$_2$O and adjusted to pH 5.0, and cultivated with shaking at 28° C. for 90 hours. The cells were collected by filtration, and washed with physiological saline. Using the resulting cells, the same reaction as in Example 1 was carried out except that the reaction time was changed to 4.5 hours. The amounts of SAH yielded are shown in Table 5.

TABLE 5

| Bacidiomycete strain | Amount of SAH yielded (micromol/ml) |
| --- | --- |
| Gloeophyllum trabeum IFO 6430 | 0.04 |
| Shizophyllum commune IFO 6504 | 0.62 |
| Trametes gibbosa IFO 4946 | 0.33 |
| Laetiporus sulphureus IFO 6497 | 0.05 |
| Lentinus edodes IFO 8340 | 0.03 |
| Lyophyllum decastes IFO 30161 | 0.11 |
| Pycnoporus coccineus IFO 9768 | 0.06 |
| Lepista nuda IFO 30139 | 0.08 |

EXAMPLE 6

One platinum loopful of *Alcaligenes faecalis* IFO 12669 cultivated on an agar slant culture medium under the same conditions as in Example 1 was inoculated in 5 ml of a liquid medium having the same composition as in Example 1 and pre-cultivated with shaking at 28° C. for 24 hours. Five milliliters of the preculture was inoculated in 500 ml of a heat-sterilized culture medium having the same composition as the pre-cultivating medium and put in a 2-liter Sagakuchi flask, and cultivated with shaking at 28° C. for 40 hours. After the main cultivation, the culture broth was washed once with physiological saline, and centrifuged to collect the resulting cells. The cells were dried at room temperature for about 15 hours while passing air, and then dried in a reduced pressure desiccator containing phosphorus pentoxide at 5° C. for 1 day. The dried product was ground by a mortar, and again dried in the reduced pressure desiccator to prepare dry cells. Fifty milligrams of the dry cells were added to 1 ml of a substrate solution composed of 2 mM of adenosine, 4 mM of DL-homocysteine and 50 mM of potassium phosphate buffer (pH 6.5). The mixture was shaken at 37° C. for 1 hour to perform reaction. The amount of SAH yielded was 1.97 micromols/ml.

EXAMPLE 7

Fifty milligrams of dry cells of each of the strains indicated in Table 6 which were prepared in the same way as in Example 6 was added to 1 ml of a substrate solution composed of 10 mM of adenosine, 10 mM of DL-homocysteine and 100 mM of potassium phosphate buffer (pH 8.0), and the mixture was shaken at 37° C. for 2 hours to perform reaction. The amounts of SAH yielded are shown in Table 6.

TABLE 6

| Strain | Amount of SAH yielded (micromol/ml) |
| --- | --- |
| Pseudomonas putida IFO 12996 | 4.62 |
| Acinetobacter calcoaceticus IFO 13006 | 3.84 |
| Alcaligenes faecalis IFO 13111 | 4.36 |

TABLE 6-continued

| Strain | Amount of SAH yielded (micromol/ml) |
| --- | --- |
| Alcaligenes faecalis IFO 12669 | 4.02 |

EXAMPLE 8

One platinum loopful of *Schizosaccharomyces pombe* IFO 0358 cultivated on an agar slant culture medium under the same conditions as in Example 2 was inoculated in 5 ml of a liquid culture medium having the same composition as in Example 2, and pre-cultivated with shaking at 28° C. for 40 hours. Then, 5 ml of the pre-culture was inoculated in 500 ml of a heat-sterilized culture medium having the same composition as the pre-cultivating medium, and cultivated at 28° C. for 40 hours. Dry cells were prepared from the culture broth by the same method as in Example 6. Using the dry cells, the same reaction as in Example 6 was carried out. The amount of SAH yielded was 1.83 micromols/ml.

EXAMPLE 9

SAH was synthesized in the same way as in Example 6 except that each of the mold fungus strains shown in Table 7 was used and the cells were collected by filtration. The results are shown in Table 7.

TABLE 7

| Mold fungus strain | Amount of SAH yielded (micromol/ml) |
| --- | --- |
| Monascus anka IAM 8001 | 1.79 |
| Mucor subtilissimus IFO 6338 | 0.51 |
| Trichophyton mentagrophytes IFO 5809 | 1.06 |
| Fusarium culmorum IFO 5902 | 0.71 |
| Sporothrix shenckii IFO 5983 | 0.42 |

EXAMPLE 10

Fifty milliliters of dry cells of *Pseudomonas putida* IFO 12996 prepared by the same method as in Example 6 were added to 1 ml of a substrate solution containing 100 mM of potassium phosphate buffer (pH 8.0) and the two substrates A and B shown in Table 8, and they were reacted at 37° C. for each of the periods shown in Table 8. The amounts of SAH yielded are shown in Table 8.

TABLE 8

| Substrate A (mM) | Substrate B (mM) | Reaction time (hr) | Amount of SAH yielded (micromol/ml) |
| --- | --- | --- | --- |
| Adenosine (5) | L-homocysteine (5) | 1.5 | 2.82 |
| Adenosine (5) | DL-homocysteine (5) | 1.5 | 2.58 |
| Adenosine (10) | L-homocystine (10) | 2 | 6.05 |
| Adenosine (10) | DL-homocystine (10) | 2 | 5.96 |
| Adenosine (200) | DL-homocysteine (200) | 20 | 87.4 |

The above results show that good results can be obtained even when DL-homocysteine, or L- or DL-homocystine was used instead of L-homocysteine.

EXAMPLE 11

Five milliliters of a culture broth of *Pseudomonas putida* IFO 12996 cultivated under the same conditions as in Example 1 except that the shaking cultivation time in the liquid medium was 20 hours and the amount of the liquid culture medium was 5 ml was inoculated in 500 ml of a heat-sterilized culture medium having the same composition as the liquid medium used in Example 1 and put in a 2-liter Sakaguchi flask, and cultivated with shaking at 28° C. for 40 hours. After the cultivation, the culture broth was centrifuged to collect the cells. The cells were washed with 0.1M potassium phosphate buffer (pH 8.0) and suspended in 10 ml of 0.1M potassium phosphate buffer (pH 8.0) containing 10 mM of dithiothreitol. The suspension was treated with ultrasonic waves at 19 KHz for 3 minutes. The treated product was centrifuged. The supernatant liquid (0.5 ml) was added to 0.5 ml of a substrate solution composed of 20 mM of adenosine, 20 mM of DL-homocysteine and 100 mM of potassium phosphate buffer (pH 8.0), and the mixture was reacted at 37° C. for 2 hours. The amount of SAH yielded was 2.70 micromols/ml.

EXAMPLE 12

Two hundred milligrams of dry cells of *Pseudomonas putida* IFO 12996 prepared by the same method as in Example 6 was suspended in ml of 10 mM potassium phosphate buffer (pH 7.0). The suspension was cooled with ice, and 375 mg of acrylamide, 20 mg of N,N'-methylenebis acrylamide and 0.25 ml of a 5% aqueous solution of N,N,N',N'-tetramethylethylenediamine were added. The resulting solution was placed under reduced pressure to drive off oxygen, and then 0.25 ml of a 2.5% aqueous solution of ammonium persulfate was added, and the solution was left to stand under ice cooling. One hour later, the resulting cell-containing gel was finely crushed and washed with 10 mM potassium phosphate buffer (pH 7.0) to prepare a cell fixed product. The fixed product (175 g) was added to 3 ml of a substrate solution composed of 20 mM of adenosine, 20 mM of DL-homocysteine and 100 mM of potassium phosphate buffer (pH 8.0), and the mixture was reacted at 30° C. for 14 hours. The amount of SAH yielded was 2.23 micromols/ml.

EXAMPLE 13

Two hundred milligrams of dry cells of *Pseudomonas putida* IFO 12996 prepared by the same method as in Example 6 was suspended in 4 ml of a substrate solution composed of 200 mM of adenosine, 200 mM of DL-homocysteine and 100 mM of $NH_4Cl—NH_4OH$ buffer (pH 9.5). The suspension was reacted at 325° C. for 30 hours. SAH was synthesized in the reaction mixture in an amount of 394 micromols (151 mg). The reaction mixture was cooled with ice, and 0.4 ml of a 30% aqueous solution of perchloric acid was added to stop the reaction. The insoluble materials such as cell residues were removed by centrifugation. The supernatant liquid was adjusted to pH 6.0 by adding 1M $KHCO_3$ aqueous solution. The resulting precipitate of potassium perchlorate was removed by centrifugation. The resulting supernatant liquid was passed through a column of Dowex 50×8 ($H^+$ type column) (a tradename for a strongly acidic cation exchange resin). The column was washed with a 0.025% aqueous solution of thiodiglycol and 2N sulfuric acid containing 0.025% thiodiglycol, and then 6N sulfuric acid containing 0.025% thiodiglycol was passed through the column. A 20% aqueous solution of phosphotungstic acid was added to the eluate, and the precipitate was collected by centrifugation and washed with cold water. It was then dissolved in 5 times its volume of acetone/water (50/50, V/V) and extracted with isoamyl alcohol/ether (1/1, V/V). The resulting aqueous layer was adjusted to pH 3.9 by adding $BaCO_3$. The resulting $BaSO_4$ was removed by filtration, and the supernatant liquid was lyophilized to give 93 mg of a white solid product. By silica gel thin-layer chromatography, high-performance liquid chromatography, paper chromatography, infrared absorption spectroscopy and specific rotation measurement, this white solid product was determined to be SAH.

EXAMPLE 14

Four hundred milligrams of dry cells of *Pseudomonas putida* IFO 12996 prepared by the same method as in Example 6 were suspended in 8 ml of a substrate solution composed of 200 mM of adenosine, 100 mM of L-homocystine and 100 mM of $NH_4Cl—NH_4OH$ buffer (pH 9.0), and the suspension was reacted at 35° C. for 25 hours. SAH was synthesized in the reaction mixture in an amount of 631 micromols (243 mg). The crude SAH was treated and purified in the same way as in Example 13 to give 149 mg of SAH as a white solid.

What is claimed is:

1. A process for producing S-adenosyl-L-homocysteine, which comprises reacting adenosine with homocysteine by contacting them in an aqueous medium in the presence of cells, crushed cells or a cell-free extract of a microorganism having the ability to synthesize S-adenosyl-L-homocysteine from adenosine and homocysteine, wherein the microorganism is *Enterobacter cloacae* IFO 13535, *Streptoverticillium kentuchense* IFO 12880, *Micropolyspora angiospora* IFO 13155, or *Microellobospor violacea* IFO 12517, and collecting the synthesized S-adenosyl-L-homocysteine.

2. A process for producing S-adenosyl-L-homocysteine, which comprises reacting adenosine with homocysteine by contacting them in an aqueous medium in the presence of cells, crushed cells or a cell-free extract of a microorganism having the ability to synthesize S-adenosyl-L-homocysteine from adenosine and homocysteine, said microorganism being selected from the group consisting of *Rhodopseudomonas spheroides* IFO 12203, *Pseudomonas putida* IFO 12996, *Pseudomonas dacunhae* IFO 12048, *Pseudomonas aeruginosa* IFO 3445, *Alcaligenes faecalis* IFO 12669, *Alcaligenes faecalis* IFO 13111, *Neurospora crassa* IFO 6067, *Fusarium culmorum* IFO 5902, *Gibberella fujikuroi* IFO 6605 *Monascus serorubescens* IFO 4487, *Monascus ruber* IFO 9203, *Monascus anka* IAM 8001, *Mucor subtilissimus* IFO 6338, *Rhizopus oryzae* IFO 5440, *Gliocladium deliquescens* IFO 6617, *Streptomyces hygroscopicus* IFO 3192, *Streptomyces griseolus* IFO 3403, *Streptoverticillium kentuchense* IFO 12880, *Micromonospora coerules* IFO 13504, *Micropolyspora angiospora* IFO 13155 and *Microellobosporia violacea* IFO 12517, and collecting S-adenosyl-L-homocysteine synthesized.

3. A process for producing S-adenosyl-L-homocysteine, which comprises reacting adenosine with homocysteine by contacting them in an aqueous medium in the presence of cells, crushed cells or a cell-free extract of a microorganism having the ability to synthesize S-adenosyl-L-homocysteine rom adenosine and homocysteine, wherein the microorganism is selected from the group consisting of *Acinetobacter calcoasceticus* IFO 12552, *Rhodopseudomonas spheroides* IFO 12203, *Sporobolomyces holsaticus* IFO 1034, *Gliocladium deliquescens* IFO 6617, *Trichophyton mentagrophytes* IFO 5809, and *Streptosporandium roseum* IFO 3776.

4. A process for producing S-adenosyl-L-homocysteine, which comprises reacting adenosine with homocysteine by contacting them in an aqueous medium in the presence of cells, crushed cells or a cell-free extract of a microorganism having the ability to synthesize S-adenosyl-L-homocysteine from adenosine and homocysteine, wherein the microorganism is *Schizosaccharomyces pombe* IFO 0346, *Neurospora crassa* IFO 6067, *Gibberella fujikuroi* IFO 6605, or *Schizophyllum commune* IFO 6504.

5. The process of claim 2 wherein the microorganism is *Pseudomonas aeruginosa* IFO 3445, *Monascus serorubesens* IFO 4487, *Monascus ruber* IFO 9203, *Streptomyces griseolus* IFO 3403 or *Streptomyces hygroscopicus* IFO 3192.

6. The process of claim 2 wherein the microorganism is *Pseudomonas dacunhae* IFO 12048 or *Monascus anka* IAM 8001.

7. The process of claim 2 wherein the microorganism if *Pseudomonas putida* IFO 12996.

8. The process of claim 2 wherein the microorganism is *Mucor subtilissimus* IFO 6338, *Fusarium culmorum* IFO 5902, *Rhizopus oryzae* IFO 5440, or *Micromonospora coerules* IFO 13504.

9. The process of claim 1 wherein the microorganism is *Alcaligenes faecalis* IFO 12669 or IFO 13111.

10. The process of claim 1 wherein said homocysteine is L-homocysteine.

11. The process of claim 1 wherein said homocysteine is Dl-homocysteine.

12. The process of claim 1 wherein the microorganism is an actinomycete.

13. The process of claim 1 wherein the microorganism is a mold fungus.

14. The process of claim 1 wherein the microorganism is a bacterium.

15. The process of claim 1 wherein the reaction is carried out at a temperature of 15° to 60° C. for a period of 0.1 to 48 hours.

16. The process of claim 1 wherein the contact is with crushed cells or a cell-free extract.

17. The process of claim 1 wherein the contact is with the cells of the microorganism which are resting cells or dry cells.

* * * * *